US012778473B2

(12) United States Patent
Marshall

(10) Patent No.: US 12,778,473 B2

(45) Date of Patent: Nov. 3, 2026

(54) THERAPEUTIC COUNTING APPARATUS

(71) Applicant: Lisa Marshall, Pembroke Pines, FL (US)

(72) Inventor: Lisa Marshall, Pembroke Pines, FL (US)

( * ) Notice: Subject to any disclaimer, the term of this patent is extended or adjusted under 35 U.S.C. 154(b) by 140 days.

(21) Appl. No.: 18/946,067

(22) Filed: Nov. 13, 2024

(65) Prior Publication Data

US 2026/0130613 A1 May 14, 2026

(51) Int. Cl.
*A61B 5/16* (2006.01)
*G06C 1/00* (2006.01)

(52) U.S. Cl.
CPC ................ *A61B 5/165* (2013.01); *G06C 1/00* (2013.01)

(58) Field of Classification Search
CPC ............ G09B 19/02; G06C 1/00; A61B 5/165
See application file for complete search history.

(56) References Cited

U.S. PATENT DOCUMENTS 3,076,272 A * 2/1963 Schott ...................... G06C 1/00 434/203
4,210,093 A 7/1980 Baker
5,451,177 A * 9/1995 Gilman ................. A63F 7/3622 446/128
8,105,088 B2 1/2012 Charles
D717,882 S * 11/2014 Chase .......................... D21/468
D719,220 S * 12/2014 Chase .......................... D21/468
2013/0052617 A1 2/2013 Harte
2013/0269594 A1 * 10/2013 Hennenfent ........... G01D 7/007 715/833
2023/0413957 A1 12/2023 Grund

FOREIGN PATENT DOCUMENTS

CN 214970818 12/2021
WO WO2020231354 11/2020

* cited by examiner

*Primary Examiner* — Jerry-Daryl Fletcher

(57) ABSTRACT

A therapeutic counting apparatus for use in a therapeutic practice to improve a user's general mood includes a positive-thought rail and a negative-thought rail mounted and spaced above a base. A plurality of positive-thought beads is slidably mounted on the positive-thought rail and a plurality of negative-thought beads is slidably mounted on the negative-thought rail. The positive-thought beads and the negative-thought beads are movable along their respective rails in the process of a therapeutic method of conditioning the brain to focus on positive thoughts and have positive emotions.

15 Claims, 4 Drawing Sheets

THERAPEUTIC COUNTING APPARATUS

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to counting apparatuses and more particularly pertains to a new counting apparatus for use in a therapeutic practice to improve a user's general mood.

(2) Description of Related Art Including Information Disclosed Under 37 CFR 1.97 and 1.98

The prior art relates to various counting apparatuses which use beads that slide on rails to count or to track myriad types of data. However, the prior art fails to describe such an apparatus in which beads are provided on a pair of rails positioned in an overlapping arrangement such that the beads may be moved according to a therapeutic method to condition the brain toward focusing on positive thoughts and having positive emotions.

BRIEF SUMMARY OF THE INVENTION

An embodiment of the disclosure meets the needs presented above by generally comprising a base which is elongated between a first end and a second end. The base has a bottom surface and a top surface and further has a front surface and a rear surface which extend between the first and second ends of the base and between the top surface and the bottom surface. A positive-thought rail is mounted to the base and is spaced upwardly from and with respect to the base. The positive-thought rail extends between the first and second ends of the base and has an inner end and an outer end with respect to the base. A plurality of positive-thought beads is slidably mounted to the positive-thought rail, wherein the positive-thought beads are movable along the positive-thought rail independently of each other.

A negative-thought rail is mounted to the base and is spaced upwardly from the base with respect to the base. The negative-thought rail extends between the first and second ends of the base and has an inner end and an outer end with respect to the base. A plurality of negative-thought beads is slidably mounted to the negative-thought rail, wherein the negative-thought beads are movable along the negative-thought rail independently of each other.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
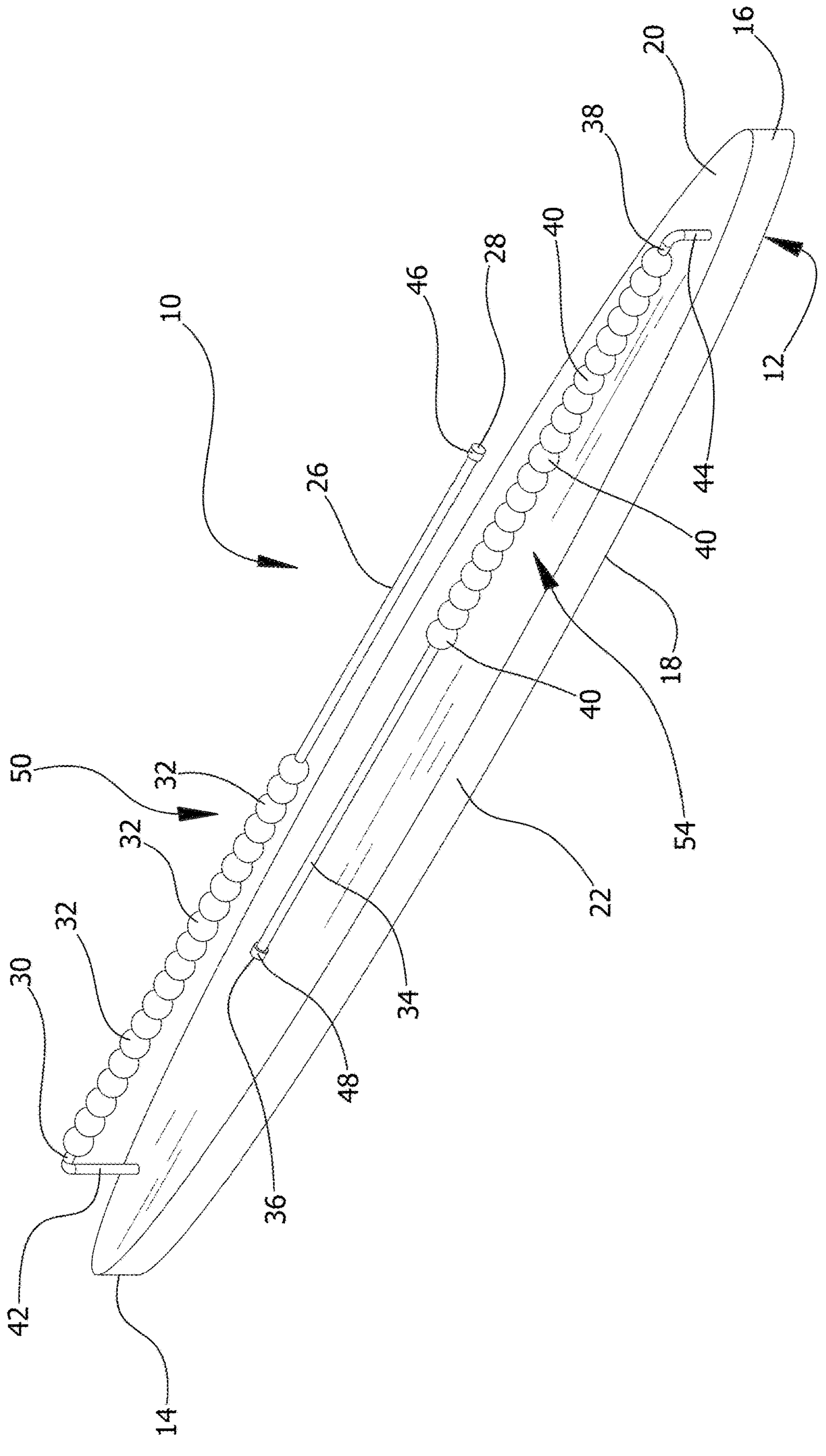
FIG. 1 is a perspective view of a therapeutic counting apparatus according to an embodiment of the disclosure.
Figure 2:
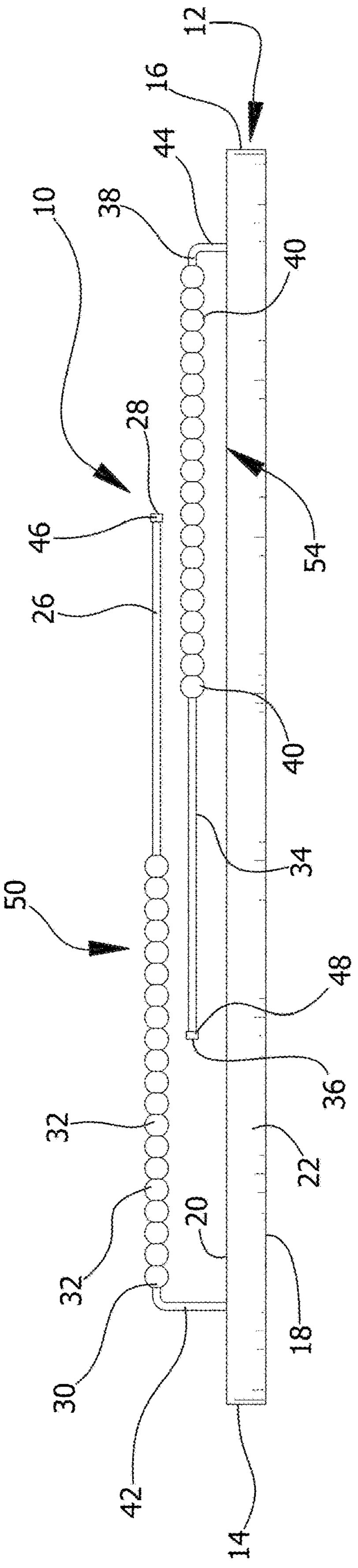
FIG. 2 is a front view of an embodiment of the disclosure.
Figure 3:
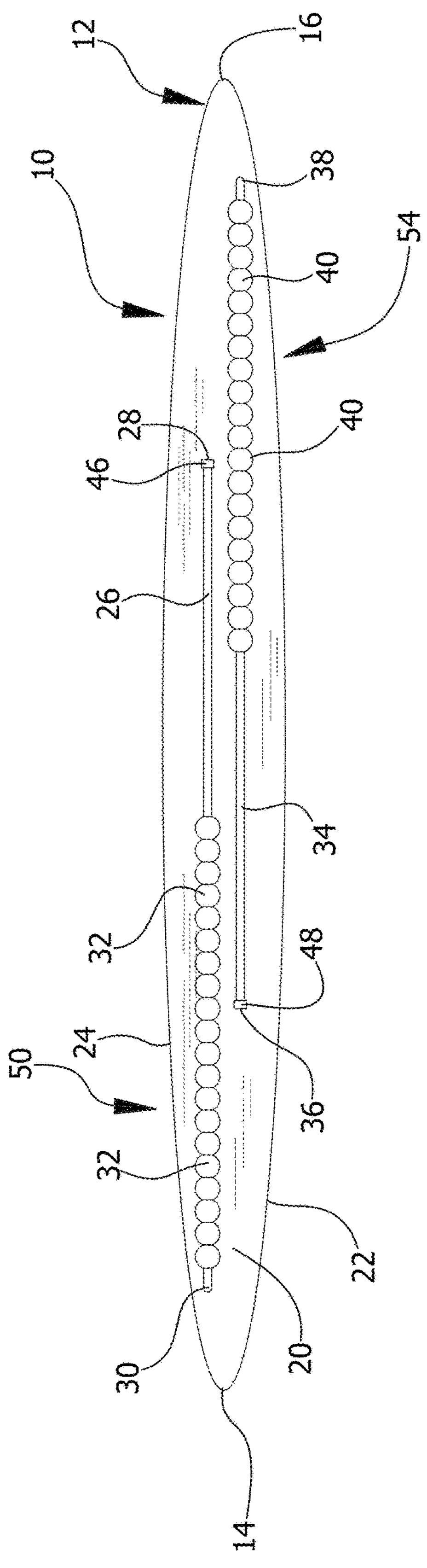
FIG. 3 is a top view of an embodiment of the disclosure.
Figure 4:
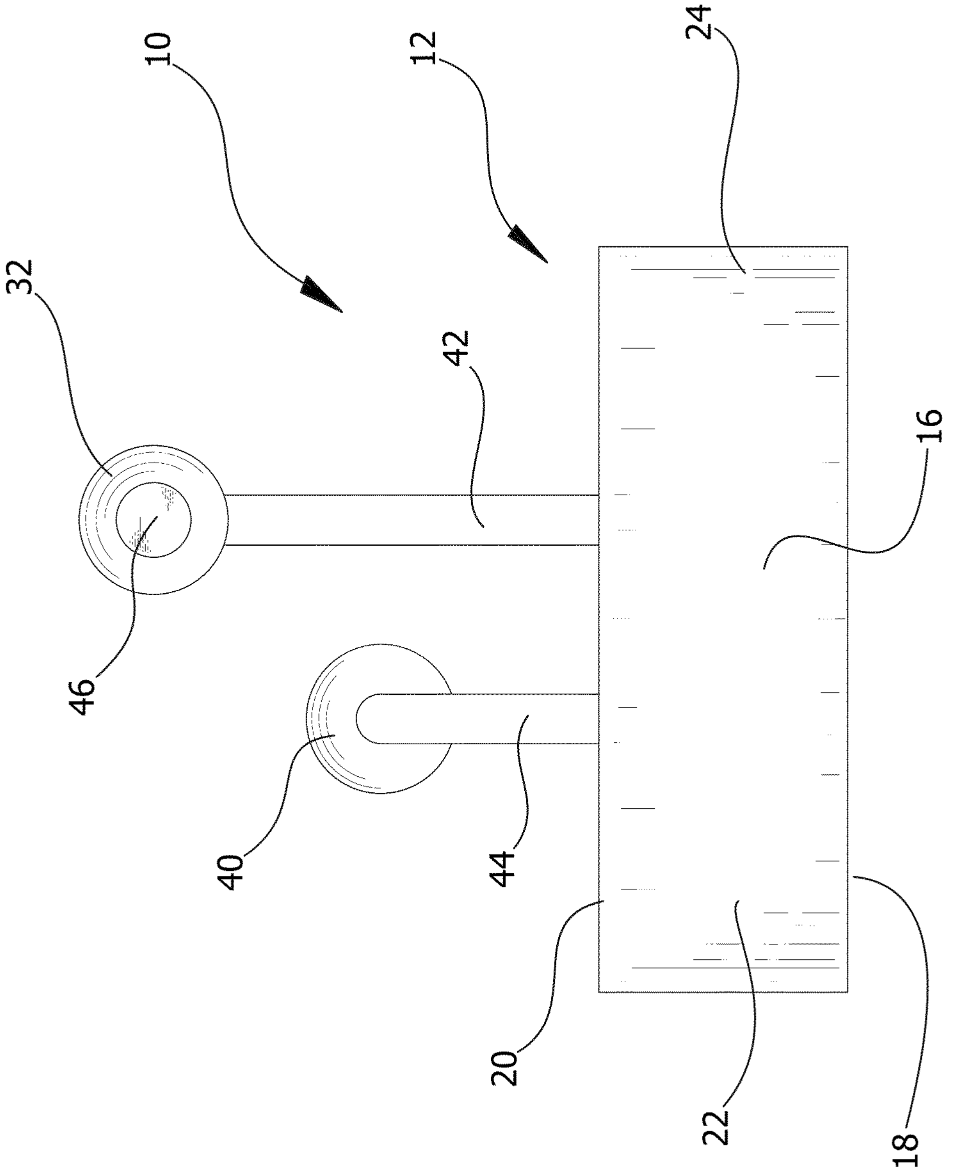
FIG. 4 is a side view of an embodiment of the disclosure.
Figure 5:
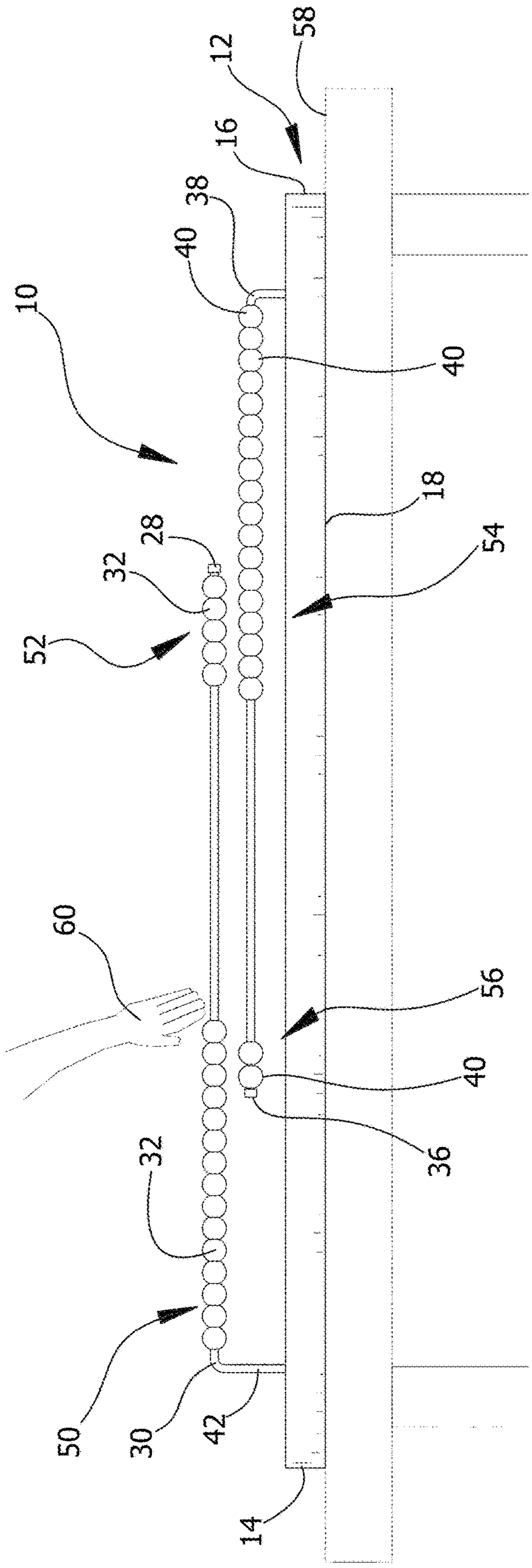
FIG. 5 is an in-use view of an embodiment of the disclosure.

With reference now to the drawings, and in particular to FIGS. 1 through 5 thereof, a new counting apparatus embodying the principles and concepts of an embodiment of the disclosure and generally designated by the reference numeral 10 will be described.

As best illustrated in FIGS. 1 through 5, the therapeutic counting apparatus 10 generally comprises a base 12 which is elongated between a first end 14 and a second end 16. The base 12 has a bottom surface 18 and a top surface 20 which are both planar and oriented parallel to each other. The base 12 has a front surface 22 and a rear surface 24 which extend between the first and second ends 14, 16 of the base 12 and between the top surface 20 and the bottom surface 18. The base 12 has an oval shape in which a major axis of the oval shape extends between the first end 14 and the second end 16.

A positive-thought rail 26 is mounted to the base 12. The positive-thought rail 26 is spaced upwardly from and with respect to the base 12. The positive-thought rail 26 is oriented to extend between the first and second ends 14, 16 of the base 12 and parallel to a central longitudinal axis of the base 12. The positive-thought rail 26 has an inner end 28 and an outer end 30 with respect to the base 12. The outer end 30 of the positive-thought rail 26 is positioned proximate to the first end 14 of the base 12. A plurality of positive-thought beads 32 is slidably mounted to the positive-thought rail 26, wherein the positive-thought beads 32 are movable along the positive-thought rail 26 independently of each other.

A negative-thought rail 34 is also mounted to the base 12. The negative-thought rail 34 is spaced upwardly from and with respect to the base 12. The negative-thought rail 34 is oriented to extend between the first and second ends 14, 16 of the base 12 and parallel to a central longitudinal axis of the base 12. The negative-thought rail 34 has an inner end 36 and an outer end 38 with respect to the base 12. The outer end 38 of the negative-thought rail 34 is positioned proximate to the second end 16 of the base 12. A plurality of negative-thought beads 40 is slidably mounted to the negative-thought rail 34, wherein the negative-thought beads 40 is movable along the negative-thought rail 34 independently of each other.

The inner end 36 of the negative-thought rail 34 is positioned closer to the first end 14 of the base 12 than the inner end 28 of the positive-thought rail 26. In other words, the positive-thought rail 26 and the negative-thought rail 34 have outer ends 30, 38 at opposite ends of the base 12 and from there past a medial plane that extends vertically through the base 12 such that inner portions of the rails overlap each other. The negative-thought rail 34 is also positioned closer to the base 12 than the positive-thought rail 26 and is positioned forwardly of the positive thought rail with respect to the base 12.

A positive-thought post 42 is coupled to and extends between the base 12 and the outer end 30 of the positive-thought rail 26. The positive-thought post 42 is integrally formed with the positive-thought rail 26. The positive-thought post 42 is oriented perpendicular to the top surface 20 of the base 12 and to the positive-thought rail 26. A negative-thought post 44 is coupled to and extends between the base 12 and the outer end 38 of the negative-thought rail 34. The negative-thought post 44 is integrally formed with the negative-thought rail 34. The negative-thought post 44 is oriented perpendicular to the top surface 20 of the base 12 and to the negative-thought rail 34.

A positive-thought stop 46 is coupled to the inner end 28 of the positive-thought rail 26 and has a size such that the positive-thought stop 46 prevents the plurality of positive-thought beads 32 from being removed from the positive-thought rail 26. Similarly, a negative-thought stop 48 coupled to the inner end 36 of the negative-thought rail 34 and has a size such that the negative-thought stop 48 prevents the plurality of negative-thought beads 40 from being removed from the negative-thought rail 34.

In use, the base 12 is placed on a support surface 58. A user 60 keeps track of the number of positive and negative thoughts the user 60 has for a given time period (e.g., one day). The thoughts tracked may be reduced to only more prominent positive and negative thoughts. In other words, fleeting thoughts or racing thoughts may be disregarded as being too inconsequential or too difficult to track. The positive-thought beads 32 are placed in an initial row 50 in which the positive-thought beads 32 are positioned in abutment with each other and against the outer end 30 of the positive-thought rail 26, while the negative-thought beads 40 are placed in their own initial row 54 in which the negative-thought beads 40 are positioned in abutment with each other and against the outer end 38 of the negative-thought rail 34.

Each time the user 60 spontaneously or otherwise has a prominent negative thought, the user 60 moves one negative-thought bead 40 from its respective initial row 54 to the inner end 36 of the negative-thought rail 34 to form or grow a terminal row 56 of negative-thought beads 40. In response, the user 60 deliberately focuses on a prominent positive thought and moves one positive-thought bead 32 from its respective initial row 50 to the inner end 28 of the positive-thought rail 26 to form or grow a terminal row 52 of positive-thought beads 32.

This process provides a means of performing a tactile action in an effort to develop a habit of thinking positive thoughts, which is intended to cause positive neurological changes in the user 60 (e.g., cause the release of neurotransmitters to improve the mood of the user 60). The habit may then condition the brain to automatically have more positive thoughts when negative thoughts occur spontaneously. The therapeutic counting apparatus 10 also provides a visual indication of the number of prominent negative thoughts and prominent positive thoughts experienced by the user 60 in the given time period as indicated by their respective terminal rows 56, 52, which may be tracked separately over the course of many such time periods with a goal of reducing the number of prominent negative thoughts had per time period.

The vertical separation of the positive-thought rail 26 and the negative-thought rail 34 facilitates viewing the positions of the positive-thought beads 32 and the negative-thought beads 40 from a variety of angles in which a viewer's eyes are positioned upwardly and forwardly of the base 12. The vertical separation also serves to indicate which rail is associated with positive thoughts and which is associated with negative thoughts (the higher rail with respect to the base 12 being the positive-thought rail 26). Other indicia such as text, graphics, colors, or the like may also be used to differentiate the positive-thought rail 26 from the negative-thought rail 34 and the positive-thought beads 32 from the negative thought beads 40.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A therapeutic counting apparatus comprising:

a base, the base being elongated between a first end and a second end, the base having a bottom surface and a top surface, the base having a front surface and a rear surface which extend between the first and second ends of the base and between the top surface and the bottom surface;

a positive-thought rail mounted to the base, the positive-thought rail being spaced upwardly from the base with respect to the base, the positive-thought rail extending between the first and second ends of the base, the positive-thought rail having an inner end and an outer end with respect to the base;

a plurality of positive-thought beads slidably mounted to the positive-thought rail, the plurality of positive-thought beads being movable along the positive-thought rail independently of each other;

a negative-thought rail mounted to the base, the negative-thought rail being spaced upwardly from the base with respect to the base, the negative-thought rail extending between the first and second ends of the base, the negative-thought rail having an inner end and an outer end with respect to the base; and a plurality of negative-thought beads slidably mounted to the negative-thought rail, the plurality of negative-thought beads being movable along the negative-thought rail independently of each other.

2. The therapeutic counting apparatus of claim 1, wherein the bottom surface of the base is planar.

3. The therapeutic counting apparatus of claim 2, wherein the top surface of the base is planar and oriented parallel to the bottom surface.

4. The therapeutic counting apparatus of claim 1, wherein the base has an oval shape.

5. The therapeutic counting apparatus of claim 1, wherein the positive-thought rail and the negative-though rail are oriented parallel to each other.

6. The therapeutic counting apparatus of claim 5, wherein the positive-thought rail and the negative-though rail are oriented parallel to a central longitudinal axis of the base.

7. The therapeutic counting apparatus of claim 1, wherein:

the outer end of the positive-thought rail is positioned proximate to the first end of the base; and the outer end of the negative-thought rail is positioned proximate to the second end of the base.

8. The therapeutic counting apparatus of claim 7, wherein the inner end of the negative-thought rail is positioned closer to the first end of the base than the inner end of the positive-thought rail.

9. The therapeutic counting apparatus of claim 1, wherein the negative-thought rail is positioned closer to the base than the positive-thought rail.

10. The therapeutic counting apparatus of claim 1, wherein the negative-thought rail is positioned forwardly of the positive thought rail with respect to the front surface of the base.

11. The therapeutic counting apparatus of claim 1, further comprising:

a positive-thought post coupled to and extending between the base and the outer end of the positive-thought rail; and a negative-thought post coupled to and extending between the base and the outer end of the negative-thought rail.

12. The therapeutic counting apparatus of claim 11, wherein:

the positive-thought post is integrally formed with the positive-thought rail; and the negative-thought post is integrally formed with the negative-thought rail.

13. The therapeutic counting apparatus of claim 11, wherein:

the positive-thought post is oriented perpendicular to the top surface of the base and to the positive-thought rail; and the negative-thought post is oriented perpendicular to the top surface of the base and to the negative-thought rail.

14. The therapeutic counting apparatus of claim 1, further comprising:

a positive-thought stop coupled to the inner end of the positive-thought rail, the positive-thought stop having a size such that the positive-thought stop prevents the plurality of positive-thought beads from being removed from the positive-thought rail; and a negative-thought stop coupled to the inner end of the negative-thought rail, the negative-thought stop having a size such that the negative-thought stop prevents the plurality of negative-thought beads from being removed from the negative-thought rail.

15. A therapeutic counting apparatus comprising:

a base, the base being elongated between a first end and a second end, the base having a bottom surface which is planar, the base having a top surface which is planar, the base having a front surface and a rear surface which extend between the first and second ends of the base and between the top surface and the bottom surface, the top surface being parallel to the bottom surface, the base having an oval shape;

a positive-thought rail mounted to the base, the positive-thought rail being spaced upwardly from the base with respect to the base, the positive-thought rail extending between the first and second ends of the base, the positive-thought rail being oriented parallel to a central longitudinal axis of the base, the positive-thought rail having an inner end and an outer end with respect to the base, the outer end of the positive-thought rail being positioned proximate to the first end of the base;

a plurality of positive-thought beads slidably mounted to the positive-thought rail, the plurality of positive-thought beads being movable along the positive-thought rail independently of each other;

a negative-thought rail mounted to the base, the negative-thought rail being spaced upwardly from the base with respect to the base, the negative-thought rail extending between the first and second ends of the base, the negative-thought rail being oriented parallel to a central longitudinal axis of the base, the negative-thought rail having an inner end and an outer end with respect to the base, the outer end of the negative-thought rail being positioned proximate to the second end of the base, the inner end of the negative-thought rail being positioned closer to the first end of the base than the inner end of the positive-thought rail, the negative-thought rail being positioned closer to the base than the positive-thought rail, the negative-thought rail being positioned forwardly of the positive thought rail with respect to the front surface of the base;

a plurality of negative-thought beads slidably mounted to the negative-thought rail, the plurality of negative-thought beads being movable along the negative-thought rail independently of each other;

a positive-thought post coupled to and extending between the base and the outer end of the positive-thought rail, the positive-thought post being integrally formed with the positive-thought rail, the positive-thought post being oriented perpendicular to the top surface of the base and to the positive-thought rail;

a negative-thought post coupled to and extending between the base and the outer end of the negative-thought rail, the negative-thought post being integrally formed with the negative-thought rail, the negative-thought post being oriented perpendicular to the top surface of the base and to the negative-thought rail;

a positive-thought stop coupled to the inner end of the positive-thought rail, the positive-thought stop having a size such that the positive-thought stop prevents the plurality of positive-thought beads from being removed from the positive-thought rail; and a negative-thought stop coupled to the inner end of the negative-thought rail, the negative-thought stop having a size such that the negative-thought stop prevents the plurality of negative-thought beads from being removed from the negative-thought rail.

* * * * *